United States Patent [19]

Funahashi et al.

[11] Patent Number: 4,696,795

[45] Date of Patent: Sep. 29, 1987

[54] TEST MEDIUM FOR DETECTING PHOSPHORUS SEGREGATES IN METALLIC MATERIAL

[75] Inventors: Yoshiko Funahashi; Yoshikazu Kamino; Yasuharu Matsumura; Senichi Harimaya, all of Chiba, Japan

[73] Assignee: Kawasaki Steel Corporation, Kobe, Japan

[21] Appl. No.: 786,286

[22] Filed: Oct. 10, 1985

Related U.S. Application Data

[62] Division of Ser. No. 670,923, Nov. 13, 1984, Pat. No. 4,643,978.

[30] Foreign Application Priority Data

Jul. 24, 1984 [JP] Japan .............................. 59-153799

[51] Int. Cl.$^4$ ........................................... G01N 31/22
[52] U.S. Cl. ....................................... 422/56; 422/68
[58] Field of Search ................ 436/78, 103, 169, 175, 436/125; 422/56, 68; 252/79.1

[56] References Cited

U.S. PATENT DOCUMENTS

| 2,676,874 | 4/1954 | Devine | 436/125 |
| 4,211,532 | 7/1980 | Tobari et al. | 422/56 |
| 4,420,567 | 12/1983 | McMahon et al. | 422/56 |

FOREIGN PATENT DOCUMENTS 22895  2/1979  Japan ................................. 436/78

OTHER PUBLICATIONS

J. Berry et al., Observations on the Use of Potassium Chromate as Indicator for the Titration of Chlorides with Silver Nitrate, The Analyst, vol. 64, 1939, pp. 730–734.

T. S. Harison, The Determination of Phosphorus in Haematite and Steel by the Molybdenum Blue Method, J.S.C.I., 68, Mar. 1949, pp. 84–88.

Primary Examiner—David L. Lacey
Attorney, Agent, or Firm—Young & Thompson

[57] ABSTRACT

A sheet impregnated with an aqueous solution of silver nitrate is effective to detect phosphorus segregates in a metallic material, particularly cast steel. Segregated phosphorus can be detected by etching a surface of steel to be tested, attaching test paper onto the steel surface, applying an aqueous solution of 0.1 to 80% by weight of silver nitrate to the test paper, maintaining the test paper in contact with the steel surface for a sufficient time, removing the test paper from the steel surface, and subjecting the test paper to fixing treatment.

6 Claims, 9 Drawing Figures

TEST MEDIUM FOR DETECTING PHOSPHORUS SEGREGATES IN METALLIC MATERIAL

This application is a division of application Ser. No. 670,923, filed Nov. 13, 1984 now U.S. Pat. No. 4,643,978.

BACKGROUND OF THE INVENTION

This invention relates to a test medium and method for detecting phosphorus segregates, and more particularly, to such a method capable of rapidly and easily detecting the distribution of phosphorus in metallic materials such as continuously cast steel slabs and large-sized steel ingots.

Heretofore, segregation in large-sized steel ingots has been judged by sulfur printing. This method is by attaching photographic paper impregnated with aqueous sulfuric acid to a polished cross section of a large-sized steel ingot, thereby detecting hydrogen sulfide given off from segregated sulfur as stains on the photographic paper. This method has been widely used on the production line. Recently, however, steels subjected to low sulfide treatment and Ca treatment, such as steels resistant to hydrogen embrittlement cracking, have been put into practical use, and much progress has been made in the art to manufacture high purity steel and to prevent segregation in continuous castings. Such advanced steels having extremely low sulfur contents are difficult to detect solidification segregates by the conventional sulphur printing.

SUMMARY OF THE INVENTION

It is an object of the invention to provide a novel improved test medium and method capable of rapidly detecting segregates in metallic materials such as Ca-loaded steels and low-sulfide steels over a large surface area as easily as by the sulfur printing. In this method, the element to be detected in place of sulfur is phosphorus, which has the great likelihood to segregate upon solidifying, and phosphorus segregates are detected on test paper as stains.

According to a first aspect of the present invention, there is provided a test medium for use in detecting phosphorus segregates in a metallic material, in the form of an aqueous solution containing 0.1 to 80% by weight of silver nitrate.

According to a second aspect of the present invention, the solution further comprises a compatible amount of an alcohol.

According to a third aspect of the present invention, there is provided a test medium for use in detecting phosphorus segregates in a metallic material, in the form of a sheet impregnated with an aqueous solution containing 0.1 to 80% by weight of silver nitrate.

According to a fourth aspect, the solution further comprises a compatible amount of an alcohol.

According to a fifth aspect of the present invention, there is provided a test medium for use in detecting phosphorus segregates in a metallic material, in the form of a sheet having an effective amount of silver nitrate incorporated therein in a dry state.

According to a sixth aspect of the present invention, there is provided a method for detecting phosphorus segregates in a metallic material, comprising (a) attaching a test sheet onto that surface of a metallic material to be tested, (b) maintaining the sheet in contact with the metallic material surface in the presence of an aqueous solution comprising 0.1 to 80% by weight of silver nitrate for a sufficient time, and (c) removing the sheet from the metallic material surface, the sheet having an image of segregates developed.

According to a seventh aspect, there is provided a method for detecting phosphorus segregates in a metallic material, comprising (a) attaching a test sheet onto that surface of a metallic material to be tested, (b) maintaining the sheet in contact with the metallic material surface in the presence of an aqueous solution comprising 0.1 to 80% by weight of silver nitrate and an alcohol for a sufficient time, and (c) removing the sheet from the metallic material surface, the sheet having an image of segregates developed.

According to an eighth aspect, the method as defined above further comprises (d) subjecting the sheet from step (c) to fixing treatment.

According to a ninth aspect, the method as defined above further comprises etching the surface of the metallic surface to be tested prior to step (a).

BRIEF DESCRIPTION OF THE DRAWINGS

The invention will be more fully understood when taken in conjunction with the accompanying drawings, in which.

DETAILED DESCRIPTION OF THE INVENTION

Figure 1:
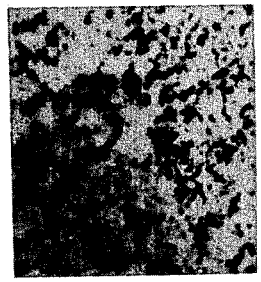
FIGS. 1 to 3 are photographic phosphorus prints representing phosphorus segregates in a continuously cast steel billet.

Like sulphur, phosphorus has the great likelihood of segregating upon solidification and is thus concentrated at the finally solidified region. Phosphorus rich portions are lower in electrochemical series and preferentially dissolved in etching solution. Ogura et al. reported in Journal of Japanese Metallurgy Associate, 45, 10, 1093 (1981), that the depth of furrows at a grain boundary in steel etched with picric acid etchant is in quantitative relationship to the quantity of phosphorus segregated at that grain boundary.

The inventors have found that by virtue of the preferential etching of phosphorus concentrated portions, phosphorus segregated on a solidified steel slab can be readily detected in a short time by introducing an aqueous solution containing 0.1 to 80% by weight of silver nitrate ($AgNO_3$) and optionally, an alcohol between that surface of the steel to be tested and a test sheet on which a pattern of phosphorus segregation is printable.

The medium for detecting segregated phosphorus may vary in form. According to a first embodiment of the present invention, the detecting medium is in the form of an aqueous solution containing 0.1 to 80% by weight of silver nitrate ($AgNO_3$) and optionally, an alcohol. On use, a dry sheet or coupon is attached onto the surface of steel to be tested and the aqueous solution is applied to the sheet as by spraying, brushing or coating to cause the solution to reach the steel surface.

According to a second embodiment of the present invention, the detecting means is in the form of a wet sheet or coupon, that is, sheet or coupon impregnated or coated with the above-mentioned aqueous solution. The wet sheet, which has contained silver nitrate and an optional alcohol in a proper amount, is ready for use, that is, it is simply attached or pressed to the surface of steel to be tested.

According to a third embodiment of the present invention, the detecting means is in the form of a dry sheet or coupon having silver nitrate born thereon in a dry state. This dry sheet is prepared by impregrating a sheet with an aqueous solution of silver nitrate followed by drying. The dry sheet is used by attaching it to the surface of steel to be tested, and applying a suitable amount of water to the sheet such that an aqueous solution containing 0.1 to 80% by weight of silver nitrate is present between the steel surface and the sheet.

In any embodiment, it is necessary that an aqueous solution containing 0.1 to 80% by weight of silver nitrate contacts the surface of steel to be tested. Solutions containing less than 0.1% by weight of silver nitrate attack the steel too weakly to detect segregated phosphorus whereas concentrations of higher than 80% weight result in deposits of the salt on the sheet to render it unuseful.

The alcohols which are optionally contained in the silver nitrate solution may be any desired alcohols, for example, methanol, ethanol, and propanol as long as they are liquid at room temperature. The conentration of alcohol in the aqueous silver nitrate solution is not particularly limited as long as the alcohol is compatible with the silver nitrate in the solution in the above-specified concentrations.

The sheets used in these embodiments may be any desired sheet-like articles of materials capable of bearing silver nitrate such as wood and synthetic resins, and preferably paper, and most preferably baryta paper, but not limited thereto.

The test sheets are attached to the surface of steel to be tested and maintained in contact with the steel surface for several minutes, for example, 3 to 10 minutes. The sheets are then removed from the steel surface and immersed in an aqueous solution of about 10 to 30% by weight of sodium thiosulfate for several minutes, for example, 5 minutes for fixing. The thus treated sheets are rinsed with running water and dried. The resulting sheets are prints clearly showing spots of segregated phosphorus as black spots.

It has been found that the silver nitrate solution with or without an alcohol serves as an etchant as well as a color producing reagent through reduction of silver. Since silver nitrate is weaker in attacking or etching action than ordinary acids, phosphorus segregated portions which are lower in natural electrode potential are preferentially dissolved and silver ions are reduced and precipitated in cooperation with the dissolution of the iron matrix, enabling detection of segregated phosphorus. Because of this mechanism, other heavy metal salts such as silver bromide, silver iodide, gold chloride and copper chloride may be used instead of silver nitrate.

The surface steel to be treated for the presence of segregated phosphorus may preferably be etched prior to the above-described detecting process. The etching solutions used for the previous etching may be solutions containing at least one of mineral acids, organic acids and salts thereof, and an alcohol. Once the surface of steel to be tested is attacked by such as etching solution, the etching solution is removed and the steel surface is subjected to the above-described testing process.

Examples of the acids include mineral acids such as hydrochloric acid, sulfuric acid, perchloric acid, phosphoric acid, nitric acid, etc.; organic acids, such as picric acid, salicylic acid, sulfosalicylic acid, acetic acid, formic acid, lactic acid, malic acid, etc.; and salts such as lithium chloride, copper chloride, calcium chloride, zinc chloride, iron chloride, aluminium chloride, copper sulfate, copper nitrate, tetramethyl ammonium chloride, etc. The alcohols which promote the attack on metal by acid may be selected from the same group as mentioned for the silver nitrate solution. The concentrations of acid and alcohol in the etching solution may vary with the characteristics of the steel surface to be tested including phosphorus concentration and the only requirement is that the alcohol is compatible with the acid in the solution.

When the steel surface to be tested is previously attacked by such a pre-etching solution, the etchant reacts with segregated phosphorus to form difficultly soluble phosphorus compounds. Upon removal of the pre-etching solution, the difficultly soluble phosphorus compounds are exposed to the ambient atmosphere to give off phosphine ($PH_3$) gas.

The silver nitrate solution is applied to the thus pre-treated surface. In the case of solutions having lower concentrations of silver nitrate above 0.1%, silver cations are reduced by $PH_3$ into metallic silver which appears as black spots or stains representing segregated phosphorus. In the case of solutions having higher concentration of silver nitrate below 80%, silver cations are directly reduced by the matrix iron to exhibit black color as in the case where the pre-etching is eliminated.

Examples of the present invention are presented below by way of illustration and not by way of limitation.

EXAMPLE 1

A steel specimen was sectioned from a segregated region of a continuously cast slab of ordinary carbon steel having a phorphorus content of 0.02% by weight. It was polished with #400 emery paper and fully cleaned with absorbent wadding. A wet test paper coupon which was impregnated with an aqueous solution of 10% by weight of silver nitrate and 50% by volume of ethanol was attached to the surface of the specimen to be tested and maintained in pressure contact for 5 minutes. The test paper having an image of segregates developed was removed from the specimen surface and fixed with an aqueous solution of 10% by weight of sodium thiosulfate. This fixing procedure is the same for the following examples. There was obtained a printed image as shown in FIG. 1.

EXAMPLE 2

Figure 2:
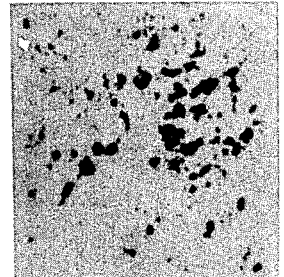

A steel specimen was taken out, polished, and cleaned in the same manner as in Example 1. A dry test paper coupon containing 6 grams of silver nitrate per square meter was attached to the surface of the specimen to be tested. Absorbent wadding full of water was forced to and moved throughout the paper such that the test paper was fully wetted with an aqueous solution of 0.1 to 80% by weight of silver nitrate. The paper was maintained in pressure contact with the speciment surface for 9 minutes. The paper was removed and fixed. There was obtained a printed image as shown in FIG. 2.

EXAMPLE 3

Figure 3:
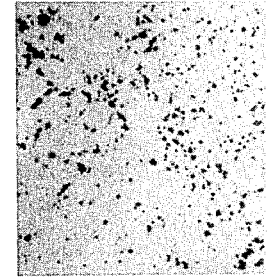

A steel specimen was taken out, polished, and cleaned in the same manner as in Example 1. A test paper coupon free of any agent was attached to the surface of the specimen to be tested. Absorbent wadding full of an aqueous solution containing 5% by weight of silver nitrate and 50% by volume of methanol was forced to and moved throughout the paper to fully wet the paper. The paper was maintained in pressure contact with the speciment surface for 7 minutes. The paper was removed and fixed. There was obtained a printed image as shown in FIG. 3.

EXAMPLE 4

Figure 4:
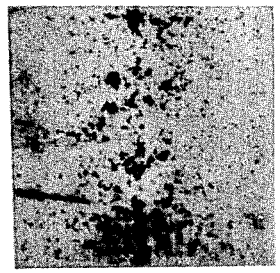
FIGS. 4 to 7 are similar photographic phosphorus prints representing phosphorus segregates in another continuously cast steel billet.

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a 5 vol % hydrochloric acid/ethanol solution for 5 minutes for etching. The etched specimen was fully cleaned with an alcohol and then a test sheet wetted with an aqueous solution containing 5% by weight of silver nitrate and 50% by volume of propanol was attached to the specimen for 3 minutes. The test sheet was removed and fixed. There was obtained a printed image as shown in FIG. 4.

EXAMPLE 5

Figure 5:
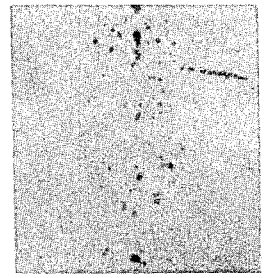

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in a saturated picric acid/ethanol solution for 5 minutes for etching. The etched speciment was fully cleaned with ethanol and then a dry test sheet containing 6 grams per square meter of silver nitrate was attached to the specimen. Water was sprayed onto the sheet to an amount of about 150 ml per square meter and the sheet was maintained in contact with the specimen surface for 3 minutes. The test sheet was removed and fixed. There was obtained a printed image as shown in FIG. 5.

EXAMPLE 6

Figure 6:
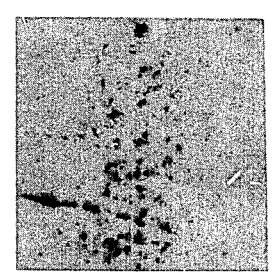

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in an ethanol solution of 5% by weight ferric chloride for 5 minutes for etching. The etched specimen was fully cleaned with ethanol and then a test sheet was attached to the specimen and wetted with an aqueous solution of 5% by weight silver nitrate and the sheet was maintained in contact with the specimen surface for 3 minutes. The test sheet was removed and fixed. There was obtained a printed image as shown in FIG. 6.

EXAMPLE 7

Figure 7:
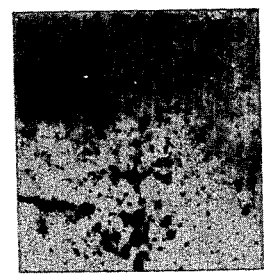

A freshly sectioned surface of a segregated region of a continuously cast slab of ordinary carbon steel having a phosphorus content of 0.02% by weight was polished with #180 emery paper and fully cleaned with absorbent wadding wetted with ethanol. The specimen was immersed in an ethanol solution of 4% by weight salicylic acid and 2% by weight of lithium chloride for 5 minutes for etching. The etched specimen was fully cleaned with ethanol and then a test sheet wetted with an aqueous solution of 5% by weight of silver nitrate was attached to the specimen and maintained in contact with the specimen surface for 3 minutes. The test sheet was removed and fixed. There was obtained a printed image as shown in FIG. 7.

Figure 8:
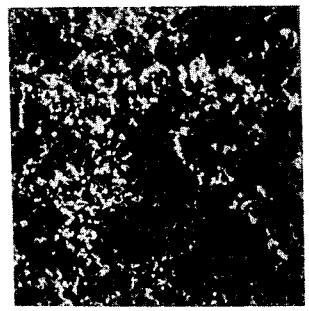
FIGS. 8 and 9 are macroanalyzer photographs showing segregated phosphorus patterns in regions corresponding to those shown in FIGS. 1-3 and FIGS. 4-7, respectively.
Figure 9:

FIGS. 8 and 9 are photographs taken on the steel slabs used in Examples 1–3 and Examples 4–7, respectively, by means of a macroanalyzer, illustrating the distribution of phosphorus thereon. With respect to the phosphorus distribution pattern on a cross section of cast steel, the printed images shown in FIGS. 1–3 and 4–7 conform to the macroanalyzer photographs of FIGS. 8 and 9, proving that the present invention is fully effective in detecting phosphorus segregation. It should be noted that the prints of FIGS. 1–3 are the mirror images of the macroanalyer photograph of FIG. 8, and the prints of FIGS. 4–7 are the mirror images of the macroanalyzer photograph of FIG. 9.

As seen from the foregoing examples, the present invention allows segregated phosphorus to be detected within several minutes after the polishing of specimens. Since no particular installation is needed for the detecting process because of the elimination of generation of any deleterious gases, the practice of the present invention is very easy during continuous steel casting in actual works. The present invention is thus very useful and benefitable in steel making. It is also very convenient that prints showing segregated phosphorus can be stored as records.

What we claim is:

1. A test medium for use in detecting phosphorus segregates in a metallic material, in the form of a sheet impregnated with an aqueous solution consisting of 0.1 to 80% by weight of silver nitrate in water.

2. The test medium according to claim 1 wherein the sheet is paper.

3. A test medium for use in detecting phosphorus segregates in a metallic material, in the form of a sheet impregnated with an aqueous solution consisting of 0.1 to 80% by weight of silver nitrate in water and alcohol.

4. The test medium according to claim 3 wherein the alcohol is a lower alkyl alcohol.

5. A test medium for use in detecting phosphorus segregates in a metallic material, consisting of a sheet having material incorporated therein in a dry state which consists of a substantial amount of silver nitrate to detect phosphorus segregates in a metallic material.

6. The test medium according to claim 5, wherein the sheet is paper.

* * * * *